US005571518A

United States Patent [19]

Pillai et al.

[11] Patent Number: 5,571,518
[45] Date of Patent: Nov. 5, 1996

[54] COSMETIC COMPOSITIONS CONTAINING TRICHOLINE CITRATE

[75] Inventors: Sreekumar Pillai, Wayne; Manisha N. Mahajan, Edgewater; Anthony V. Rawlings, Wyckoff, all of N.J.

[73] Assignee: Chesebrough-Pond's USA Co., Division of Conopco, Inc., Greenwich, Conn.

[21] Appl. No.: 546,959

[22] Filed: Oct. 30, 1995

[51] Int. Cl.⁶ ............................. A61K 7/42; A61K 7/06; A61K 7/48
[52] U.S. Cl. ........................... 424/401; 424/59; 424/70.1
[58] Field of Search ........................... 424/401, 59, 70.1

[56] References Cited

U.S. PATENT DOCUMENTS

| | | | |
|---|---|---|---|
| 2,865,938 | 12/1958 | Rosenfelder | 260/439 |
| 3,395,229 | 7/1968 | Feigh et al. | 424/295 |
| 4,275,059 | 6/1981 | Flora et al. | 424/204 |
| 4,816,568 | 3/1989 | Hamilton et al. | 530/399 |
| 5,166,139 | 11/1992 | Bombardelli et al. | 514/26 |
| 5,244,665 | 9/1993 | Natraj et al. | 424/401 |
| 5,376,646 | 12/1994 | Pittrof et al. | 514/78 |
| 5,391,550 | 2/1995 | Carniglia et al. | 574/23 |

OTHER PUBLICATIONS van Scott et al., "Control of Keratinization with α-Hydroxy Acids and Related Compounds", *Arch. Dermatol.*, vol. 110, Oct. 1974, pp. 586–590.
Berardesca et al., "AHA Mechanisms of Action", *Cosmetics & Toiletries*, vol. 110, Jun. 1995, pp. 30–31.
Abstract of DE 4 310 015.
Abstract of JP 6179613.
Abstract of SU 1811403.
Abstract of EP 0 479 121.

*Primary Examiner*—John C. Bleutge
*Assistant Examiner*—Margaret Glass
*Attorney, Agent, or Firm*—Rimma Mitelman

[57] ABSTRACT

Cosmetic compositions containing tricholine citrate (TCC). TCC stimulates keratinocyte growth, does not inhibit keratinocyte differentiation and increases the phospholipid levels in keratinocytes. Thus, TCC provides improved conditioning, improved youthful appearance, moisturization and improvement in the appearance of photodamaged skin.

4 Claims, No Drawings

COSMETIC COMPOSITIONS CONTAINING TRICHOLINE CITRATE

FIELD OF THE INVENTION

The invention relates to a composition suitable for topical application to human skin for the treatment and conditioning of the skin and for reducing the damaging effects of UV light on human skin, containing an effective amount of tricholine citrate.

BACKGROUND OF THE INVENTION

Tricholine citrate (hereinafter "TCC") is an ester of citric acid with three choline molecules.

Citric acid is a hydroxy tricarboxylic acid. Since the discovery by van Scott et al., "Control of Keratinization with α-Hydroxy Acids and Related Compounds", Arch. Dermatol., Vol. 110, October 1974, pp. 586–590, that hydroxyacids are effective for the treatment of hyperkeratotic disorders of the skin, several hydroxy acids and related compounds have been used extensively in dermatologic and cosmetic preparations. The reported cosmetic properties of hydroxy acids include improved skin texture, improved skin brightness and firmness, decreased wrinkling and decreased pigmentation. See e.g., Berardesca et al., "AHA Mechanisms of Action", Cosmetics & Toiletries, Vol. 110, June 1995, pp. 30–31.

Triesters of citric acid with alkyl or aryl groups have been claimed to have anti-aging and UV protecting effects. See e.g., Natraj et al., U.S. Pat. No. 5,244,665. Triethyl and tributyl esters of citric acid have been shown to be effective in the treatment of photodamaged and/or hyperpigmented skin, and in slowing down the aging process, in addition to the photoprotective action. The use of TCC, however, has not been taught or suggested for use in skin treatment compositions. Natraj et al. do not appear to teach or suggest either TCC or any nitrogen or amine-containing citrate esters.

Choline is an essential nutrient for phospholipid, sphingolipid and sphingomyelin biosynthesis in all cells. In addition, choline acts as a methyl donor for carnitine biosynthesis which is required for normal fatty acid turnover. Choline deficiency results in reduced lipoprotein biosynthesis, decreased membrane turnover and increased triglyceride accumulation. Choline deficiency in the epidermis could result in lower barrier lipid formation leading to an abnormal water barrier and poor skin condition. Choline in the form of phosphatidyl choline or phosphoryl choline and their derivatives have been used in cosmetic compositions and have been claimed to have multiple beneficial effects on skin, such as anti-fungal effects, wound healing enhancers, dry skin benefits, improving transepidermal water loss, moisturizing effects, anti-acne effects, UV protecting effects, conditioning benefits, humectant effects, and anti-inflammatory effects. See U.S. Pat. No. 5,391,550; U.S. Pat. No. 5,376,646; Abstract of German Patent Application No. 4 310 015; Abstract of Japanese Patent Specification No. 6179613; Abstract of Soviet Union Patent Specification No. 1811403; Abstract of European Patent Application No. 0 479 121; U.S. Pat. No. 5,166,139. Patented compounds include phosphatidyl choline, phosphoryl choline, acylated choline, sphingomyelin or their derivatives.

Choline salicylate has been employed as an anti-inflammatory and analgesic agent for topical use. See U.S. Pat. No. 4,275,059 (Flora et al.).

TCC is a common inexpensive chemical used in the past as an effective iron chelator. See Rosenfelder, U.S. Pat. No. 2,865,938. TCC has been used to stabilize animal growth hormone preparations (see Hamilton et al., U.S. Pat. No. 4,816,568) and to treat iron deficiency anemia (see Feigh et al., U.S. Pat. No. 3,395,229). No toxicity or adverse effects have been associated with this molecule since its individual components, citric acid and choline, are naturally occurring metabolites in cells.

Skin treatment or cosmetic compositions containing tricholine citrate have not been disclosed. None of the art described above teaches the use of TCC for the growth of skin cells or skin cell cultures. Furthermore, the art does not appear to teach or suggest the use in cosmetic compositions of any citrate ester wherein citric acid is esterified with any compound which serves as an essential nutrient for skin cells.

The top layer of human skin or the epidermis is composed of many different cell types including keratinocytes, melanocytes and langerhans cells. Keratinocytes are the major cell type of the epidermis (75–80% of the total number of cells in the human epidermis). Within the epidermis the keratinocytes reside in four distinct stages of differentiation. The basal layer rests on the basal lamina separating epidermis from the dermis. These cells are large columnar rapidly proliferating cells. These basal cells migrate upward within the epidermis, initiated by the process of differentiation. The layer above the basal cells is the spinous layer. The cells in the spinous layer initiate the production of proteins characteristic of the differentiated epidermis. The granular layer, lying above the spinous layer, is characterized by electron-dense granules. This layer is responsible for the synthesis of lipid molecules required for the formation of the water impermeable barrier of the skin. The topmost layer of the skin, the stratum corneum, is formed from the granular layer by the destruction of cellular organelles. The cells in the stratum corneum, corneocytes, contain extensively cross-linked proteins, surrounded by a highly resistant cell envelope. The corneocytes are embedded in a bed of specific lipid structures (analogous to bricks on a bed of mortar) and this structure provides the protective barrier for the skin. The outermost layer of corneocytes is peeled off from the skin during the normal process of desquamation. Differentiation of the epidermal keratinocytes is the driving force for the normal desquamation process to occur. Epidermal differentiation is important for providing the essential function of the skin, namely to provide a protective barrier against the outside environment and to prevent loss of water from the body. The rate of synthesis of DNA, determined by the incorporation of radiolabeled substrate [$^3$H]thymidine, is an indicator of keratinocyte proliferation. An increase in cornified envelopes and the enzyme transglutaminase, which is responsible for the formation of cornified envelopes, indicates an increase in keratinocyte differentiation. The basal cells which have the highest rate of growth, are the least differentiated. The most differentiated cells of the stratum corneum do not have the ability to proliferate. The increased proliferation of the basal cells is the driving force for the differentiation of the upper layer cells to form corneocytes.

The present invention is based, in part, on the discovery that TCC induces cell proliferation and increases cellular lipid levels in skin, both of which in turn result in increased benefits to skin, such as improved conditioning, improved youthful appearance, decrease in wrinkle appearance, moisturizing, and improvement in the appearance of photodamaged skin.

Accordingly, it is an object of the present invention to provide compositions for the treatment of skin using TCC as the active ingredient.

It is another object of the invention to provide a method for treating the appearance of wrinkled, flaky, aged, or photodamaged skin and for promoting youtful appearance.

These and other objects of the invention will become more apparent from the detailed description and examples which follow.

SUMMARY OF THE INVENTION

The invention provides a composition suitable for topical application to human skin, the composition containing as an essential ingredient, from 0.0001 to 50 wt. % of tricholine citrate and a cosmetically acceptable vehicle for tricholine citrate.

The vehicle enables tricholine citrate (TCC) to be dispersed onto the skin and distributed therein. According to the invention, TCC is employed to increase keratinocyte proliferation and to increase phospholipid levels in keratinocytes, in order to improve skin appearance.

The present invention also includes a method of improving or preventing the appearance of wrinkled, dry, flaky, aged, photodamaged skin and treating skin disorders (e.g., acne or psoriasis), which method includes applying to the skin a composition containing TCC.

Compositions of the invention are intended for topical application to mammalian skin which is already in dry, flaky, wrinkled, aged, photodamaged condition or which suffers from a skin disorder, or, in the alternative, the inventive compositions may be applied prophylactically to normal healthy skin to prevent or reduce the deteriorative changes.

DESCRIPTION OF THE PREFERRED EMBODIMENT

Tricholine citrate is an essential ingredient of the inventive compositions. Tricholine citrate has the following structure:

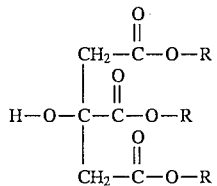

where R represents a choline molecule having the structure

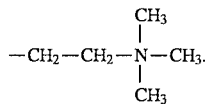

In general, the amount of TCC in the inventive compositions is in the range of from about 0.0001% to about 50% by weight of the composition. Preferably, in order to lower cost and maximize the effect, the amount of TCC is in the range of from about 0.01% to about 10%, most preferably in the range of from 0.1% to 5%.

COSMETICALLY ACCEPTABLE VEHICLE

The composition according to the invention also comprises a cosmetically acceptable vehicle to act as a dilutant, dispersant or carrier for the TCC in the composition, so as to facilitate its distribution when the composition is applied to the skin.

Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the emulsion, and can, in the absence of other cosmetic adjuncts, form the balance of the composition.

OPTIONAL SKIN BENEFIT MATERIALS AND COSMETIC ADJUNCTS

An oil or oily material may be present, together with an emulsifier to provide either a water-in-oil emulsion or an oil-in-water emulsion, depending largely on the average hydrophilic-lipophilic balance (HLB) of the emulsifier employed.

In a preferred embodiment of the invention, the inventive compositions further include at least one of the following ingredients which are particularly effective in combination with TCC.

Ceramides and/or other sphingolipids may be included in the inventive composition. Suitable ceramides and synthetic analogues thereof are disclosed in European Patent Application 534 286, European Patent Application 227 994, U.S. Pat. No. 5,175,321, U.S. Pat. No. 4,985,547, U.S. Pat. No. 5,028,416, U.S. Pat. No. 5,071,971, Japanese Patent Application No. 63192703, U.S. Pat. No. 4,468,519 and U.S. Pat. No. 4,950,688, all of which are incorporated by reference herein. Sphingolipids, including ceramides or their synthetic analogues, may be present in the inventive compositions at a level of from about 0.00001 to about 5%, preferably from about 0.00001 to about 1%, optimally from about 0.01 to 0.5%.

Hydroxyacids are preferably included in the inventive compositions to enhance proliferation and to increase ceramide biosynthesis in keratinocytes, increase epidermal thickness, and increase desquamation of normal skin resulting in smoother, younger looking skin.

The hydroxy acid can be chosen from α-hydroxy acids, β-hydroxyacids, other hydroxycarboxylic acids (e.g., dihydroxycarboxylic acid, hydroxy-dicarboxylic, hydroxytricarboxylic) and mixtures thereof or combination of their stereoisomers (DL, D or L).

Preferably the hydroxy acid (ii) is chosen from α-hydroxy acids having the general structure:

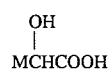

where M is H— or $CH_3(C_fH_g)_h$—, f is an integer of from 1 to 27, g is an integer of from 2 to 54, and h is 0 or 1.

Even more preferably, the hydroxy acid is chosen from 2-hydroxyoctanoic acid, hydroxylauric acid, lactic acid, and glycolic acid, and mixtures thereof. When stereo isomers exist, L-isomer is most preferred.

The keto acids can be chosen from α-keto acids, β-keto acids and mixtures thereof.

A particularly preferred α-keto acid is 2-keto octanoic acid.

Preferably the amount of the hydroxy acid present in the composition according to the invention is from 0.01% to 20%, more preferably from 0.05% to 10% and most preferably from 0.1% to 3% by weight.

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmirate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials available under the trademark Carbopol® from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents, skin anti-wrinkling agents, anti-dandruff agents, anti-acne agents and hair growth stimulants.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxy-cinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds.

Powders may be incorporated into the cosmetic composition of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

USE OF THE COMPOSITION

The composition according to the invention is intended primarily as a product for topical application to human skin, especially as an agent for reducing the permeability to water of the skin, particularly when the skin is dry or damaged, in order to reduce moisture loss and generally to enhance the quality and flexibility of skin and to improve the appearance of photodamaged skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

PRODUCT FORM AND PACKAGING

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,507, incorporated by reference herein.

The following specific examples further illustrate the invention, but the invention is not limited thereto.

METHODS

Cell Culture

Human keratinocytes, isolated from neonatal foreskin by trypsin treatment were grown in Dulbecco Modification Eagle (DME) Hams F12 (3:1) medium/5% fetal calf serum in the presence of mitomycin C treated 3T3 mouse fibroblasts for establishing dividing keratinocyte colonies. Cells were grown under the above condition until their second passage and kept frozen for future use. Frozen second passage keratinocytes were thawed and plated into the above medium and grown for five days. On day 5, when the cells were 70–80% confluent, they were trypsinized and plated in the serum-free medium for the various experiments.

METHODOLOGY USED FOR DETERMINING THE RATE OF DNA SYNTHESIS IN KERATINOCYTES

The incorporation of $^3$H-thymidine by cultured keratinocytes was used as an assay of keratinocyte proliferation. Thymidine is one of four deoxynucleosides which are the monomeric units of DNA, the universal library of genetic information in the animal kingdom. Prior to cell division of a somatic cell such as a keratinocyte, the complete genome of the cell undergoing cell division is replicated. This involves large scale DNA synthesis by the cell and enables both daughter cells to receive identical copies of the genetic material. When $^3$H-thymidine is included in the culture media of keratinocytes which are synthesizing DNA in preparation for cell division then the labelled nucleoside is incorporated into the newly synthesized DNA. The extent of incorporation of $^3$H-thymidine into a population of cells is proportional to the rate of DNA synthesis by this population of cells and therefore an indication of their cellular proliferation.

1. Normal human keratinocytes isolated from neonatal foreskins by trypsin treatment were grown in DME medium/5% fetal calf serum in the presence of mitomycin C treated 3T3 mouse fibroblasts for establishing dividing keratinocyte colonies. Keratinocytes were grown under the above condition until their third passage.

2. For the experiments, third passage keratinocytes were plated into a serum-free keratinocyte growth medium (KGM; obtained from Clonetics, San Diego, Calif.) containing 0.09 mM calcium. 20,000 to 30,000 cells were plated into each well of 24 well cell culture plates and grown for 5 days, until the cells reach about 80% confluence.

3. Medium was changed to fresh medium and the various test materials were added to the medium from an ethanolic stock solution. The final ethanol concentration in the cultures was kept below 0.2%. Control cultures received no tested material but were dosed with 0.2% ethanol. Each compound or combination was tested in three separate wells. In four hours, 1 uCi of $^3$H-thymidine (Amersham Corp., Sp activity 40 Ci/mmol) was added to the 1 ml medium in each well. The cells were incubated overnight and 24 hours later the amount of $^3$H-thymidine associated with the cellular DNA of keratinocytes was assessed as described below.

4. The medium was aspirated, and the wells washed with 1 ml phosphate-buffered saline. The DNA and proteins of the cells in the plate were then precipitated by adding 1 ml of ice-cold 10% trichloroacetic acid (TCA). The plates were left on ice for 30 minutes to complete the precipitation process. TCA was then aspirated and each well was then washed four times with 5% TCA. The plates were then dried on a filter pad and the cells in the wells were dissolved in 0.5 ml of 0.1N sodium hydroxide. The sodium hydroxide was then neutralized using 0.1N hydrochloric acid and the solution (1 ml total volume) was then transferred to a scintillation vial. 50 μl samples from each vial were used for protein assay using BCA protein assay reagent obtained from Pierce Chemical Company. 8 ml of a scintillation fluid (Ecolume) was added to the rest of the solution in the vial, and the vials were counted in a scintillation counter to determine the amount of radioactivity in each vial. The DNA synthesis rate was then calculated as cpm $^3$H thymidine incorporated into total cellular DNA/microgram of cell protein for each individual well. Mean and standard deviation for each group was also calculated. These numbers were also expressed as percent of control wells which did not receive any test compound.

5. TCC was obtained from Sigma Chemical Co.

METHODOLOGY FOR TRANSGLUTAMINASE MEASUREMENT

During the process of terminal differentiation in the epidermis, a 15 nm thick layer of protein, known as the cornified envelope (CE) is formed on the inner surface of the cell periphery. The CE is composed of numerous distinct proteins which have been cross-linked together by the formation of N $^\epsilon$-(-γ-glutamyl) lysine isodipeptide bonds catalyzed by the action of at least two different transglutaminases expressed in the epidermis. Transglutaminase (TG-1) is expressed in abundance in the differentiated layers of the epidermis, especially the granular layer, but is absent in the undifferentiated basal epidermis. Thus, TG-1 is a useful marker of epidermal keratinocyte differentiation with high TG-1 levels indicating a more differentiated state. An ELISA based TG-1 assay, using a TG-1 antibody, was used to assess the state of differentiation of the cultured keratinocytes in the examples that follow.

The level of TG-1 was measured as follows. Keratinocytes grown in 96 well plates were treated for 72 hours with a test compound and the cells were frozen at −20° C. for TG-1 assay. The DNA content of the cells in the wells were first determined before the TG-1 assay.

After aspirating the medium and washing the plate once with PBS, DNA content of the plates was quantitated by the DNA binding flurophore, bisbenzimidazole (Hoescht 33258) and measuring the specific fluoresceace of the DNA-bound flurophore at 450 nm (excitation at 360 nm).

TG-1 levels of the cells in the wells were determined using the TG-1 specific monoclonal antibody (BC1) (first antibody) (obtained from Amersham Life Sciences) and using a peroxidase labelled rabbit antimouse IgG fragment (second antibody). The plates were blocked by 5% nonfat milk in TBS (Tris buffered saline, pH 8.0) for one hour followed by overnight incubation with the first antibody (1:2,000 fold dilution) in 1% milk/TBS at 4° C. After rinsing the plates three times with 1% milk/TBS containing 0.05% Tween 20, the plates were incubated with 1:4000 dilution of the second antibody at room temperature for two hours. The plates were rinsed three times with 1% milk/TBS/Tween and three times with TBS. Color was developed by incubation with o-phenylene diamine and hydrogen peroxide. The optical density was read at 410 nm in a microtiter plate reader and the TG-1 levels were calculated as OD/DNA fluorescence. The mean ±Standard Deviation of at least six separate wells were used for calculation and statistical analysis of the data. Results are expressed as % of control.

METHODOLOGY FOR ANALYSIS OF LIPID LEVELS

The cells after the treatments with tested compounds were washed two times with PBS, and mechanically scraped from the dishes into 1.8 mL of 0.88% KCl for lipid extraction using chloroform:methanol (1:1). The chloroform phase was separated, dried under nitrogen, and resuspended in 200 μl of chloroform for separation of the different lipid classes by column chromatography.

Aminopropyl columns (Waters division of Millipore) were washed with 3 mL of chloroform:isopropanol (2:1) followed by 2 mL of hexane to condition the column. The lipid samples were applied onto the column and the different lipid classes were separated using the following solvent systems: 2 ml of hexane:ethyl acetate (85:15) to elute the non-polar lipids (cholesterol and cholesterol esters); and 2 ml of chloroform:isopropanol (2:1) to elute the neutral lipids (ceramides, cerebrosides, and monoglycerides) and 2 mls of 2% acetic acid in methanol to extract polar lipids (phospholipids and fatty acids).

Total cholesterol was quantitated using the cholesterol assay kit obtained from Sigma. Phospholipid quantitation in the neutral and polar lipid fractions were carried out by spotting the lipids onto High Performance Thin Layer Chromatography (HPTLC) silica gel plates and running in chloroform:methanol: acetic acid (47.5:2.25:0.25). Quantitation was performed by immersing the HPTLC plates in a solution containing 10% Copper Sulfate and 8% Phosphoric acid and charring at 165° C. for 15 minutes. Micrograms of phospholipids remaining at the origin in the extract were determined by reflectance densitometry and comparison with phospholipid standards.

ANALYSIS OF $^3$H CHOLINE INCORPORATION INTO PHOSPHOLIPIDS OF KERATINOCYTES

Choline acts as an essential nutrient for the cellular phospholipid biosynthesis of keratinocytes. Choline present in the medium is used up by the cells for phospholipid biosynthesis. If TCC provides choline for the cells it will complete with the choline in the medium for incorporation into cellular phospholipids. When cells are incubated with $^3$H-labelled choline, its incorporation into phospholipids will be decreased by the presence of unlabelled choline or TCC in the medium. Thus, a decrease in the $^3$H choline incorporation into phospholipids indicates that TCC provides choline for keratinocyte lipid biosynthesis.

Keratinocytes grown to 80% confluence was treated with the different agents (choline, citrate, TEC, TBC or TCC) and labelled with 1 uCi/ml media of $^3$H labelled choline (obtained from Amersham) for 24 hours. The wells were washed, total lipids were extracted using Bleigh Dyer method as described above and the total counts in the chloroform phase was determined. To ascertain that the counts are present only in the phospholipid fraction, the amount of $^3$H choline incorporated into the different lipid fractions were quantitated by running TLC of the fractions in the above solvent system, and the amount of radioactivity in the phospholipid fraction (origin) was quantitated using BioScan plate reader. The cpm of $^3$H choline was plotted against the amount of cold choline or TCC added in the medium to assess the competition between choline supplied from TCC with $^3$H choline.

EXAMPLE 1

Effect of Citrate Esters on Keratinocyte Proliferation

Effects of 24 hours exposure to 0.1 μM to 10 mM of citric acid, choline or the different citrate esters on keratinocyte DNA synthesis are shown in table 1. Rate of DNA synthesis calculated as cpm $^3$H thymidine incorporated into cellular DNA/μg of cell protein is expressed as % of control (no addition controls) ±SD. The actual amount of cpm/μg protein of the control is 1103 ±88.

TABLE 1

| (μM) | Citric acid | Choline | TCC | TEC | TBC |
|---|---|---|---|---|---|
| 0 | 100 ± 7.9 | 100 ± 7.9 | 100 ± 7.9 | 100 ± 7.9 | 100 ± 7.9 |
| 0.1 | 88.4 ± 15.5 | 125 ± 17.6 | 92.4 ± 6.8 | 112 ± 21.5 | 106 ± 8.4 |
| 1.0 | 74.5 ± 32.2 | 113 ± 12.0 | 97.7 ± 25.6 | 112 ± 13.1 | 100.0 ± 28 |
| 10 | 89.9 ± 20.3 | 109 ± 3.3 | 91.0 ± 14.0 | 79.1 ± 13.9 | 68.2 ± 13 |
| 100 | 88.7 ± 5.1 | 114 ± 12.0 | 94.5 ± 13.4 | 9.8 ± 2.3* | 8.7 ± 5.5* |
| 1000 | 63.9 ± 11.8 | 115 ± 24.0 | 102 ± 12.3 | 11.2 ± 9.2* | 1.35 ± .1* |
| 10,000 | 4.25 ± 2.2* | 127 ± 10.7 | 19.7 ± 9.8* | 1.2 ± 0.02* | 0.505 ± 0* |

*statistically significant compared to controls.
[1]triethylcitrate
[2]tributylcitrate The results indicate that all agents, except choline, at 10 mM levels inhibited DNA synthesis of keratinocytes. Both TEC and TBC were inhibitory above 10 μM. TCC had no growth inhibitory effects up to 1 mm. This study indicates that TCC is tolerated better than other citrate esters by keratinocytes in vitro, perhaps due to the choline present in the TCC. Choline even at 10 mM levels was in fact slightly growth stimulatory, in contrast to all the other agents tested. TBC and TEC were inhibitory at lower concentrations than citric acid and at or above 1 mM levels the cells showed signs of cytotoxicity in the presence of TBC or TEC.

The aged epidermis may be choline deficient due to the decreased capillary circulation to the skin. To simulate the choline-deficient in vitro system, keratinocytes were plated in complete medium and 48 hours later switched to choline-free medium. The cells were then grown for five days in the choline-free medium with or without addition of different amounts of choline or TCC. To determine whether TCC can provide choline for keratinocyte proliferation under these conditions, on day 5, the amount of $^3$H thymidine incorporation into DNA was determined as in the previous experiment. The protein content of the wells were also quantitated. Both these parameters were expressed as % of control ±SD. The actual amount of DNA synthesis and protein content for the controls were 14584 ±1737 cpm/μg protein and 21 ±4 μg protein/well respectively.

TABLE 2

| (μM) | DNA (Choline) | DNA (TCC) | Protein (Choline) | Protein (TCC) |
|---|---|---|---|---|
| 0 | 100 ± 11.9 | 100 ± 6.3 | 100 ± 21.6 | 100 ± 18.6 |
| 1 | 261 ± 5.6* | 345 ± 15.2* | 197 ± 21.8* | 233 ± 18.3* |
| 10 | 313 ± 11.4* | 319 ± 38.4* | 264 ± 50* | 229 ± 37* |
| 100 | 315 ± 29.3* | 332 ± 34.2* | 276 ± 52* | 215 ± 18* |
| 1000 | 297 ± 11.3* | 187 ± 35.0* | 229 ± 29* | 120 ± 29* |
| 10,000 | 270 ± 11.2* | 13.8 ± 0.9* | 209 ± 13.7* | 23 ± 1.5* |

*statistically significant compared to control.

It can be seen from Table 2 that both choline and TCC increased the proliferation of keratincoytes (both DNA synthesis and protein content) at as low a concentration as 1 μM. Only the highest concentration of TCC (10 mM) inhibited DNA synthesis, all other concentrations of TCC stimulated keratinocyte growth significantly in a choline-free medium. This indicates that choline from TCC becomes available to the cells for the synthesis of essential phospholipids required for the cell membrane synthesis.

EXAMPLE 2

Effects of Citrate Esters on Keratinocyte Differentiation

Proper skin conditioning require enhanced proliferation and differentiation of epidermal keratinocytes. The different citrate esters were tested on their effect on cornified envelope (CE) formation, a marker of terminal differentiation of keratinocytes. Citrate esters were tested at 1 mM levels in medium containing 0.15 mM Ca. Levels are expressed as % of control ±SD. The CE formation for the control was 54.48 ±31.8 cpm/μg cell protein.

TABLE 3

| Agents | Choline | Citric acid | TCC | TBC | TEC |
|---|---|---|---|---|---|
| CE Levels (% Control) | 135 ± 23.6 | 13.7 ± 1.1* | 91.3 ± 54.0 | 23.6 ± 2.1* | 18.6 ± 4.2* |

*statistically significant effects

The data in Table 3 clearly indicates that choline increased cornified envelope formation whereas TCC had no effect. However, citric acid and other citrate esters all inhibited cornified envelope formation significantly. Thus, this data show that TCC is clearly superior to citric acid or other citrate esters in its effect on keratinocyte differentiation, i.e., TCC does not inhibit keratinocyte differentiation whereas other citrate esters do. As seen in Example 1 for the proliferation, choline content of TCC may protect it from the differentiation inhibitory effects of citric acid, whereas the other esters of citric acid are not protected.

Cornified envelope formation is determined by the activity of transglutaminase enzyme which cross-links all the envelope precursor proteins to form the envelope. This enzyme is calcium dependent and is inhibited by calcium chelators such as citric acid and citric acid esters. However, cornified envelope formation was not affected by TCC. To understand the reason for this, we determined the effect of different citrate esters on transglutaminase I levels in keratinocytes after 48 hour treatment with different amounts of the agents.

TABLE 4

| (μM) | Choline | TCC | TBC | TEC |
|---|---|---|---|---|
| 0 | 100 ± 15 | 100 ± 15 | 100 ± 15 | 100 ± 15 |
| 1 | 121.8 ± 18 | 98.2 ± 4.5 | 100 ± 13 | 77.3 ± 10.7 |
| 10 | 124.2 ± 8.7* | 94.5 ± 17 | 79 ± 13 | 76.7 ± 20.8 |
| 100 | 120.4 ± 11.3* | 89.5 ± 14.2 | 79 ± 13 | 67.2 ± 11.9* |

*statistically significant effects compared to controls.

As seen in Table 4, choline stimulated transglutaminase while TBC and TEC inhibited the enzyme. TCC had no significant effect on this enzyme. Therefore, it appears that the negative effect of citrate on transglutaminase is counteracted by the stimulatory effect of choline of TCC. This may be the reason for the neutral effect of TCC on keratinocyte differentiation while both TBC and TEC inhibited differentiation. Thus, TCC increases proliferation and does not inhibit differentiation of keratinocytes whereas citric acid and other citrate esters inhibit both proliferation and differentiation of keratinocytes. Furthermore, choline, a nutrient component of TCC, enhances differentiation, suggesting TCC is clearly superior to other citrate esters for keratinocyte proliferation and differentiation.

EXAMPLE 3

Effect of Citrate Esters on Keratinocyte Lipid Synthesis

To demonstrate directly that choline from TCC is incorporated into phospholipids of keratinocytes, cells were labelled with 1 uCi $^3$H choline/ml medium for 48 hours in the presence of different concentrations of the different citrate esters, citric acid or choline. The amount of $^3$H choline incorporated into cellular phospholipids was determined and expressed as % of controls. The amount of $^3$H choline incorporated into phospholipid fraction in the control was 252 ±cpm/μg protein

TABLE 5

| (μM) | Citric acid | Choline | TCC | TBC | TEC |
|---|---|---|---|---|---|
| 0 | 100 ± 16.5 | 100 ± 16.5 | 100 ± 16.5 | 100 ± 16.5 | 100 ± 16.5 |
| 10 | 91.4 ± 12.7 | 61.6 ± 7.8* | 67.9 ± 8.9* | 81.1 ± 7.0 | 114 ± 9.9 |
| 100 | 77.5 ± 19.5 | 36.9 ± 1.6* | 20.8 ± 0.3* | 120.7 ± 6.7 | 89.2 ± 1.9 |
| 1000 | 74.1 ± 28.8 | 10.8 ± 5.5* | 4.5 ± 1.9* | 81.1 ± 12.0 | 82.8 ± 22 |

*statistically significant effects compared to controls.

The data indicate that both choline and TCC compete with $^3H$ choline for incorporation into cellular phospholipids. Choline competition is expected since it is competing with the same molecule (the only difference is in the $^3H$ label) for incorporation. The fact that TCC acts similar to choline is a direct demonstration that choline from TCC becomes available to cells for cellular phospholipid synthesis. Other esters of citric acid and citrate itself have no significant effect on choline incorporation into phospholipid fraction.

To determine whether TCC treated cells have higher levels of lipids the following experiment shown in Table 6 was conducted. Keratinocytes were treated with different concentrations of TCC for 48 hours and the lipid levels of the cells were quantified. The amounts of cholesterol, fatty acids and phospholipids were quantified and expressed as % of control. Amount of cholesterol was 7.34 ±0.14, fatty acid was 21.4 ±2.5 and phospholipid was 5.8 ±1.26 ng/μg cell protein.

TABLE 6

Cholesterol, fatty acid and phospholipid levels of keratinocytes treated with TCC

| (μM) | Cholesterol | Fatty acids | Phospholipids |
|---|---|---|---|
| 0 | 100 ± 1.85 | 100 ± 12.2 | 100 ± 21.7 |
| 1 | 85.3 ± 10.2 | 96.9 ± 8.2 | 77.1 ± 9.3 |
| 10 | 111.2 ± 24.1 | 83.9 ± 6.8 | 112.4 ± 24.4 |
| 100 | 78.3 ± 21.7 | 79.1 ± 12.4 | 148.2 ± 26.5* |
| 1000 | 69.3 ± 3.7* | 76.7 ± 16.7 | 187.2 ± 9.3 |

*statistically significant effects compared to controls.

The data in Table 6 indicates that TCC increased the phospholipid levels of keratinocytes without affecting the levels of other lipids. This is to be expected since TCC provides choline which preferentially gets incorporated into cellular phospholipids.

All the above described examples clearly demonstrate that TCC is more beneficial than other esters of citric acid in providing growth, differentiation and lipid synthetic benefits to keratinocytes. In summary, examples described here confirm that tricholine citrate is superior to other esters of citric acid and has the potential to deliver superior anti-aging, skin conditioning and UV protecting benefits. This compound has the advantage that it is composed of two essential metabolites required by the body, is broken down rapidly within skin cells to its individual components, deliver the individual benefits of its two components and is safe and non-toxic even at high concentrations.

EXAMPLE 4

This example illustrates a high internal phase water-in-oil emulsion incorporating the inventive composition.

| | % w/w |
|---|---|
| TCC | 0.5 |
| 1,3-dimethyl-2-imidazolidinone | 0.2 |
| Brij 92* | 5 |
| Bentone 38 | 0.5 |
| $MgSO_4 7H_2O$ | 0.3 |
| Butylated hydroxy toluene | 0.01 |
| Perfume | qs |
| Water | to 100 |

*Brij 92 is polyoxyethylene (2) oleyl ether

EXAMPLE 5

This example illustrates an oil-in-water cream incorporating the inventive composition.

| | % w/w |
|---|---|
| TCC | 2 |
| Mineral oil | 4 |
| 1,3-dimethyl-2-imidazolidinone | 1 |
| Brij 56* | 4 |
| Alfol 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 6

This example illustrates an alcoholic lotion incorporating the composition according to the invention.

| | % w/w |
|---|---|
| TCC | 5 |
| 1,3-dimethyl-2-imidazolidinone | 0.1 |
| Ethanol | 40 |
| Perfume | qs |
| Butylated hydroxy toluene | 0.01 |
| Water | to 100 |

EXAMPLE 7

This example illustrates another alcoholic lotion containing the inventive composition.

| | % w/w |
|---|---|
| TCC | 10 |
| 1,3-dimethyl-2-imidazolidinone | 0.01 |
| Ethanol | 40 |
| Antioxidant | 0.1 |
| Perfume | qs |
| Water | to 100 |

EXAMPLE 8

This example illustrates a suncare cream incorporating the composition of the invention:

| | % w/w |
|---|---|
| TCC | 2 |
| 1,3-dimethyl-2-imidazolidinone | 0.2 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 9

This example illustrates a non-aqueous skin care composition incorporating the inventive combination.

| | % w/w |
|---|---|
| TCC | 5 |
| 1,3-dimethyl-2-imidazolidinone | 1 |
| Silicone gum SE-30[1] | 10 |
| Silicone fluid 345[2] | 20 |
| Silicone fluid 344[3] | 50.39 |
| Squalene | 10 |
| Linoleic acid | 0.01 |
| Cholesterol | 0.03 |
| 2-hydroxy-n-octanoic acid | 0.7 |
| Vitamin E linoleate | 0.5 |
| Herbal oil | 0.5 |
| Ethanol | 2 |

[1]A dimethyl silicone polymer having a molecular weight of at least 50,000 and a viscosity of at least 10,000 centistokes at 25° C., available from GEC
[2]Dimethyl siloxane cyclic pentamer, available from Dow Corning Corp.
[3]Dimethyl siloxane tetramer, available from Dow Corning Corp.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A method of enhancing keratinocyte proliferation in skin, the method comprising applying to the skin composition comprising from 0.0001 to 50 wt. % by weight of the composition of tricholine citrate and a cosmetically acceptable vehicle.

2. A method for treating the appearance of wrinkled, dry, flaky, aged, or photodamaged skin comprising applying to the skin a composition comprising from 0.0001 to 50 wt. % by weight of the composition of tricholine citrate and a cosmetically acceptable vehicle.

3. A method of enhancing phospholipid levels in skin keratinocytes, the method comprising applying to the skin a composition comprising from 0.0001 to 50 wt. % by weight of the composition of tricholine citrate and a cosmetically acceptable vehicle.

4. A topical composition comprising from 0.0001 to 50 wt. % by weight of the composition of tricholine citrate, a cosmetically acceptable vehicle, and an additional cosmetic ingredient selected from the group consisting of an alpha hydroxy acid, a sunscreen, a tanning agent, a skin anti-wrinkling agent, an anti-dandruff agent, an anti-acne agent, a hair growth stimulant and a perfume.

* * * * *